United States Patent
Hayek

(10) Patent No.: US 8,565,855 B2
(45) Date of Patent: *Oct. 22, 2013

(54) MRI METHOD

(76) Inventor: Zamir Hayek, London (GB)

( * ) Notice: Subject to any disclaimer, the term of this patent is extended or adjusted under 35 U.S.C. 154(b) by 384 days.

This patent is subject to a terminal disclaimer.

(21) Appl. No.: 12/367,774

(22) Filed: Feb. 9, 2009

(65) Prior Publication Data

US 2010/0041980 A1 Feb. 18, 2010

Related U.S. Application Data

(62) Division of application No. 10/362,868, filed on Aug. 4, 2003, now Pat. No. 7,509,157.

(51) Int. Cl.
*A61B 5/05* (2006.01)
*A61M 16/00* (2006.01)
*A62B 7/00* (2006.01)

(52) U.S. Cl.
USPC ....... 600/413; 128/200.24; 600/421; 600/415

(58) Field of Classification Search
USPC ........ 600/413, 421, 415; 128/200.24, 204.18; 607/42

See application file for complete search history.

(56) References Cited

U.S. PATENT DOCUMENTS

| | | | |
|---|---|---|---|
| 4,397,306 A | 8/1983 | Weisfeldt et al. | |
| 4,958,637 A | 9/1990 | Aritomi | |
| 4,971,042 A | 11/1990 | Lerman | |
| 5,363,844 A | 11/1994 | Riederer et al. | |
| 5,377,671 A | 1/1995 | Biondi et al. | |
| 5,513,647 A | 5/1996 | Castile | |
| 6,295,465 B1 | 9/2001 | Simonetti | |
| 6,535,754 B2* | 3/2003 | Fishbein et al. | 600/422 |
| 6,580,938 B1 | 6/2003 | Acker | |
| 6,595,211 B2* | 7/2003 | Weiler et al. | 128/204.18 |
| 6,597,939 B1 | 7/2003 | Lampotang et al. | |
| 7,006,862 B2* | 2/2006 | Kaufman et al. | 600/523 |
| 7,616,981 B2* | 11/2009 | Taniguchi et al. | 600/410 |

FOREIGN PATENT DOCUMENTS

| | | |
|---|---|---|
| JP | 7299111 A | 11/1995 |
| WO | WO00/22985 | 4/2000 |

OTHER PUBLICATIONS

Kahler E et al: "Quantitative regional blood volume studies in rat myocardium in vivo" Magnetic Resonance in Medicine, Oct. 1998, vol. 40, No. 4, pp. 517-525, XP002180926, ISSN: 0740-3194, Williams & Wilkins, USA.

Grove J R et al: "Modified Ventilator with Logic Controller for Cardiorespiratory Synchronisation of Magnetic Resonance Imaging in Small Animals" Medical and Biological Engineering and Computing, vol. 33, No. 1, 1995, pp. 104-107, XP000486797, ISSN: 0140-0118, Peter Peregrinus Ltd. Stevenage, GB.

* cited by examiner

*Primary Examiner* — Jacqueline Cheng

(74) *Attorney, Agent, or Firm* — Colin P. Cahoon; Celina M. Orr; Carstens & Cahoon, LLP

(57) ABSTRACT

A method of operating a magnetic resonance imaging scanner for imaging the heart of a patient comprising inducing apnoea in the patient; sensing an electrical heart waveform; in response thereto moving the chest wall of the patient to a desired location; and triggering the scanner to image.

9 Claims, 3 Drawing Sheets

MRI METHOD

CROSS-REFERENCE TO RELATED APPLICATION

This application is a divisional patent application of U.S. Ser. No. 10/362,868 filed on Aug. 4, 2003, entitled "MRI Method," the technical disclosure of which is hereby incorporated herein by reference.

FIELD OF THE INVENTION

The present invention relates to a method and apparatus for magnetic resonance imaging and more particularly but not exclusively to a magnetic resonant imaging in coronary and vascular angiography.

BACKGROUND OF THE INVENTION

Coronary artery disease is a major killer in Western Society. Evaluation of patients having suspected coronary artery disease is therefore desirable. The conventional techniques include diagnostic catheterization and X-ray angiography. Both techniques have inherent risk to the patient and have cost and time implications which are becoming increasingly unacceptable.

SUMMARY OF THE INVENTION

It is desirable to use non-invasive techniques where possible. A promising technique is magnetic resonance imaging. Such a technique requires successive data collection phases to generate successive slice images.

A major difficulty with magnetic resonance imaging of coronary arteries is the need to perform a large number of imaging steps with a patient who is likely to move, at least due to breathing.

It is normal to perform the imaging steps during breath holds of the patient, but this does not solve the problem of variability as the patient is likely to hold his breath at different chest positions with each breath hold. To ameliorate the problems breath-coaching has been performed in an attempt to minimize variability of respiratory motion. Regardless of the success in terms of minimizing respiratory motion, such techniques are inconvenient to the patient and time-consuming for both the patient and medical staff.

Advances in software do allow for some movement between different imaging steps but it is widely recognised that to achieve high resolution with minimal artefacts it would best to image with consistent chest position.

It would also be advantageous to perform the successive imaging steps with the chest in its deflated state so as to minimize the separation between the chest and the heart.

According to a first aspect of the present invention there is provided a method of operating a magnetic resonance imaging scanner for imaging a portion of the coronary arteries of a patient comprising:

inducing apnoea in the patient;
sensing an electrical heart waveform and,
in response thereto moving the chest wall of the patient to a desired location and triggering the scanner to image.

Preferably the step of moving the chest wall of the patient to a desired location comprises providing an enclosure around at least the chest of the patient and applying gas at a predetermined pressure to said enclosure.

According to a second aspect of the present invention a method of operating a magnetic resonance imaging scanner for imaging a portion of the coronary arteries of a patient, comprising:

inducing apnoea in the patient;
sensing an electrical heart waveform;
in response thereto, applying pressure to the exterior of the chest of the patient to produce expiration; and thereafter
triggering the scanner to image.

Preferably the method further comprises providing a structure for engaging at least the chest of the patient, said structure having a sealing device for at least partially sealing to the chest, and disposing said structure in engagement with said chest thereby defining with said chest a pressure chamber, and wherein said step of inducing apnoea comprises applying cyclic pressure changes to said pressure chamber to cause hyperventilation of said patient.

Advantageously the step of applying cyclic pressure changes comprises selecting a desired magnitude of pressure at a blower and successively reversing a connection of said blower to said chamber to thereby successively apply a positive pressure and a negative pressure.

Conveniently the method further comprises feeding back a pressure in said chamber to control the output of said blower.

According to a third aspect of the present invention there is provided a magnetic resonance imaging device comprising a magnetic resonance imaging scanner, a structure in use engaging at least the chest of a patient to define, with said chest, a pressure chamber, a respirator device for applying cyclically varying pressures to said chamber to cause cyclic forced respiration of said patient, said forced respiration comprising successive inspiration and expiration periods, and plural electrodes connected to said respirator device and said magnetic resonance imaging scanner for sensing an electrical waveform of the heart of said patient thereby triggering said magnetic resonance imaging scanner in accordance with said waveform, and a discriminator device for triggering said forced respiration in accordance with a predetermined point of said waveform.

Preferably said discriminator device is operable to determine the time period between successive maximum electrical amplitudes of said waveform, and further comprises variable timing circuitry for setting a triggering instant as a proportion of said time period.

Advantageously said discriminator device is operable to provide a trigger pulse in response to a predetermined characteristic of said waveform.

Conveniently said respirator device comprises a blower in use inducing air at an inlet and propelling said air from an outlet, a valve having a valve member and a body, said body having a first port connected to said inlet, a second port connected to said outlet, a third exhaust port connected to the ambient air and a fourth port connected to said chamber and a drive motor for moving said valve member with respect to said body for selecting between a first state in which said first port is connected to said fourth port and said second port is connected to said third exhaust port, and a second state in which said second port is connected to said fourth port and said first port is connected to said third port.

Preferably said drive motor is further operable to move said valve member to a third position is which said third port and said fourth ports are connected together, and said first and second ports are both closed.

Conveniently said respirator device comprises control circuitry for said drive motor.

Advantageously said control circuitry comprises said discriminator device.

Preferably said respirator further comprises a blower drive motor connected to said control circuitry whereby said control circuitry is operable to set a desired output pressure from said blower.

Advantageously said respirator has a pressure feedback transducer having an output connected to said control circuitry for regulating the pressure output by said blower.

Preferably said control circuitry comprises a digital processor.

According to a fourth aspect of the present invention there is provided a ventilator for artificial respiration comprising a blower having an air inlet and an air outlet, a valve having a first port connected to said inlet, a second port connected to said outlet, a third port connected as exhaust and a fourth port for connection to a structure in use defining at least a part of a ventilator chamber for a chest of a patient, a first drive device for operating said blower and a second drive device for operating said valve and further comprising control circuitry for controlling said second drive device to provide cyclic connections between said fourth port and said first and second ports, the ventilator yet further comprising a connection device for ECG leads, discrimination circuitry for detecting a selected electrical event at said connection device and in response thereto for supplying a control signal to said control circuitry for causing the operation of said second drive device at a predetermined time relationship to said electrical event.

Preferably said discrimination circuitry is operable to determine the time period between successive maximum electrical amplitudes of said waveform, and further comprises variable timing circuitry for setting a triggering instant as a proportion of said time period.

Advantageously said discrimination circuitry is operable to provide a trigger pulse in response to a predetermined characteristic of said waveform.

Preferably said respirator device comprises a blower in use inducing air at an inlet and propelling said air from an outlet, a valve having a valve member and a body, said body having a first port connected to said inlet, a second port connected to said outlet, a third exhaust port connected to the ambient air and a fourth port connected to said chamber and a drive motor for moving said valve member with respect to said body for selecting between a first state in which said first port is connected to said fourth port and said second port is connected to said third exhaust port, and a second state in which said second port is connected to said fourth port and said first port is connected to said third port.

Conveniently said drive motor is further operable to move said valve member to a third position is which said third port and said fourth ports are connected together, and said first and second ports are both closed.

Conveniently again said respirator device comprises control circuitry for said drive motor.

Advantageously said control circuitry comprises said discriminator device.

Preferably the respirator further comprises a blower drive motor connected to said control circuitry whereby said control circuitry is operable to set a desired output pressure from said blower.

Preferably again said respirator has a pressure feedback input connected to said control circuitry for regulating the pressure output by said blower.

Advantageously said control circuitry comprises a digital processor.

BRIEF DESCRIPTION OF THE DRAWINGS

An embodiment of the invention will now be described, by way of example only, with reference to the accompanying drawings in which.

In the various figures, like reference numerals refer to like parts.

DETAILED DESCRIPTION OF THE PREFERRED EMBODIMENTS

Figure 1:
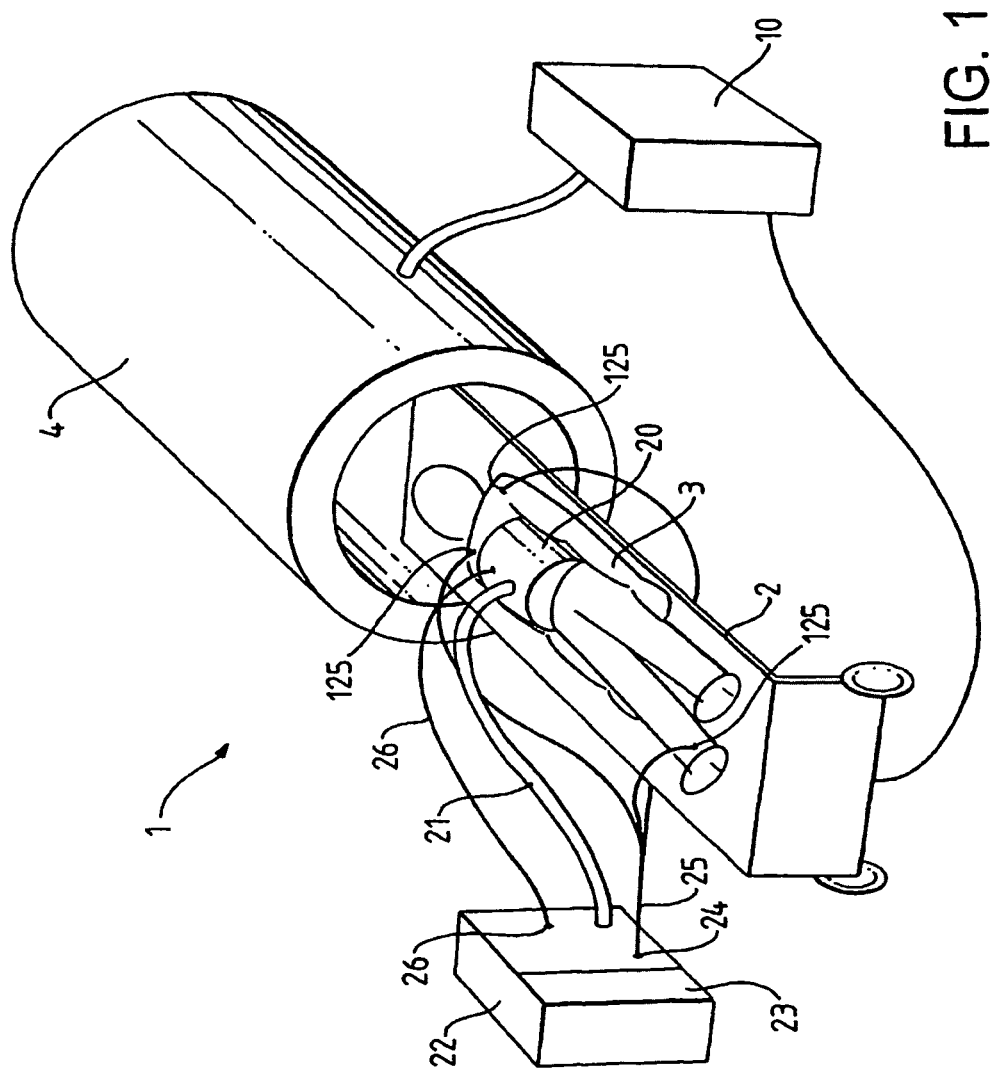
FIG. 1 shows a partial view of an MRI scanner with a patient connected to an apparatus for artificial respiration in accordance with an embodiment of the invention.

Referring first to FIG. 1 an MRI scanner 1 has a patient table 2 supporting a patient 3 so as to move the patient between the coils 4 of the scanner. As is known to those skilled in the art, the coils 4 typically comprise powerful magnets producing a $B_0$ field for the imaging procedure, gradient coils for producing a gradient in the $B_0$ field in X, Y and Z directions and an RF coil for producing a $B_1$ field for spin rotation. Certain of the coils are toroidal so that the patient 3 is surrounded by the coils 4. The RF coil also detects the signal from spins within the body.

A computer control unit 10 controls the position of the patient by moving the table, controls the radio frequency supplied to the coil units and pulses for the coil unit.

Secured to the patient's chest is a cuirass 20, which together with associated sealing means forms a pressure chamber surrounding at least the chest of the patient. The cuirass is connected via large diameter tubing 21 to a ventilator device 22 which is capable of providing pulses of positive and negative pressure with respect to ambient under the control of a control section 23. The ventilator device 22 has a connection point 24 for ECG leads 25 which have electrodes 125 secured to the patient typically at 3 locations. Narrow diameter tubing 26 feeds back the pressure in the pressure chamber to the ventilator device 22, so that a desired pressure regime can be created, at a pressure transducer input 26.

Figure 2:
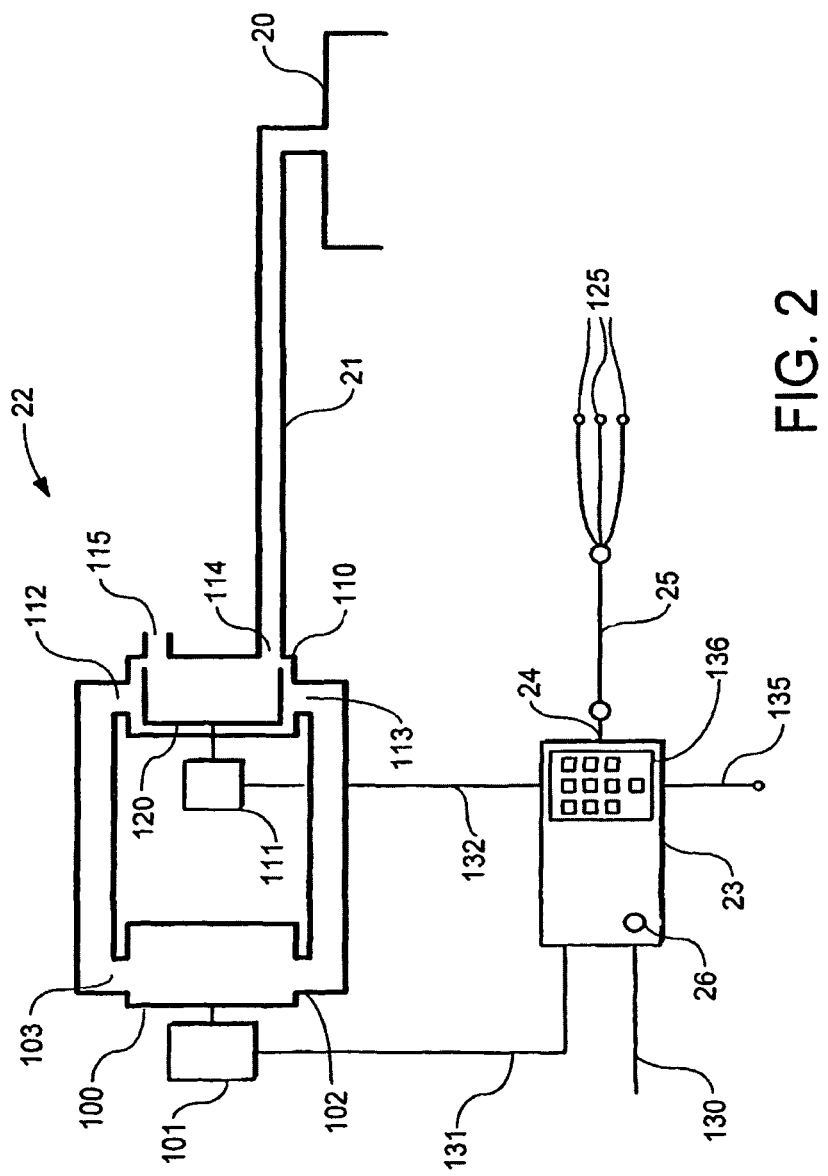
FIG. 2 shows a first embodiment of a ventilator for producing artificial respiration and controlling an MRI scanner.

Referring now to FIG. 2, the ventilator in this embodiment consists of a blower 100 driven by an electric motor 101 and constantly moving air from an inlet port 102 to an outlet port 103. The inlet and outlet ports connect to a valve 110 driven by an electric servo or stepper motor 111. The valve 110 has four ports, namely a positive pressure port 112, a negative pressure 113 an outlet port 114 and an exhaust port 115. The positive pressure port 112 is connected to the outlet port 103 of the blower 100. The negative pressure port 113 is connected to the inlet port 102 of the blower 100. A valve member 120 has a first position in which it connects the low pressure port to the outlet port 114 and the high pressure port 112 to the exhaust 115, and a second position in which it connects the high pressure port 112 to the outlet port 114 and the low pressure port 113 to the exhaust 115.

Preferably the valve includes further positions intermediate the first and second positions and intermediate the second and first positions in which both ports 113 and 112 are closed and the outlet port 114 is connected to the exhaust port 115.

The valve may be of the type described in our co-pending patent application No. PCT GB98/01317 or other valves may be used instead.

The outlet port 114 is connected to the cuirass 20 via the large diameter tubing 21.

The control section 23 receives power from a power lead 130 and has an output power lead 131 for driving the blower drive motor 101. In the preferred embodiment this motor is speed-controlled by the control section 23 in accordance with pressure fed back to pressure transducer input 26 and a pressure set-point.

The control section 23 has a second output lead 132 for controlling the valve motor 111 preferably both in speed and position. The control section 23 contains processing circuitry so that the valve may operate to provide cyclically varying positive and negative pressure in the cuirass 20 (when sealingly engaged with the patient's chest), or may for example maintain the valve in a single position for a substantial period of time—for example—providing constant negative or constant positive pressure to the chest of a patient.

The control section, as previously discussed, is responsive to ECG leads 25 connected to the control port 24 and further has an ECG trigger output line 135 for connection to an MRI scanner.

In an alternative embodiment, ECG leads and an ECG sensor in the MRI scanner are used to provide the necessary triggering.

Figure 3:
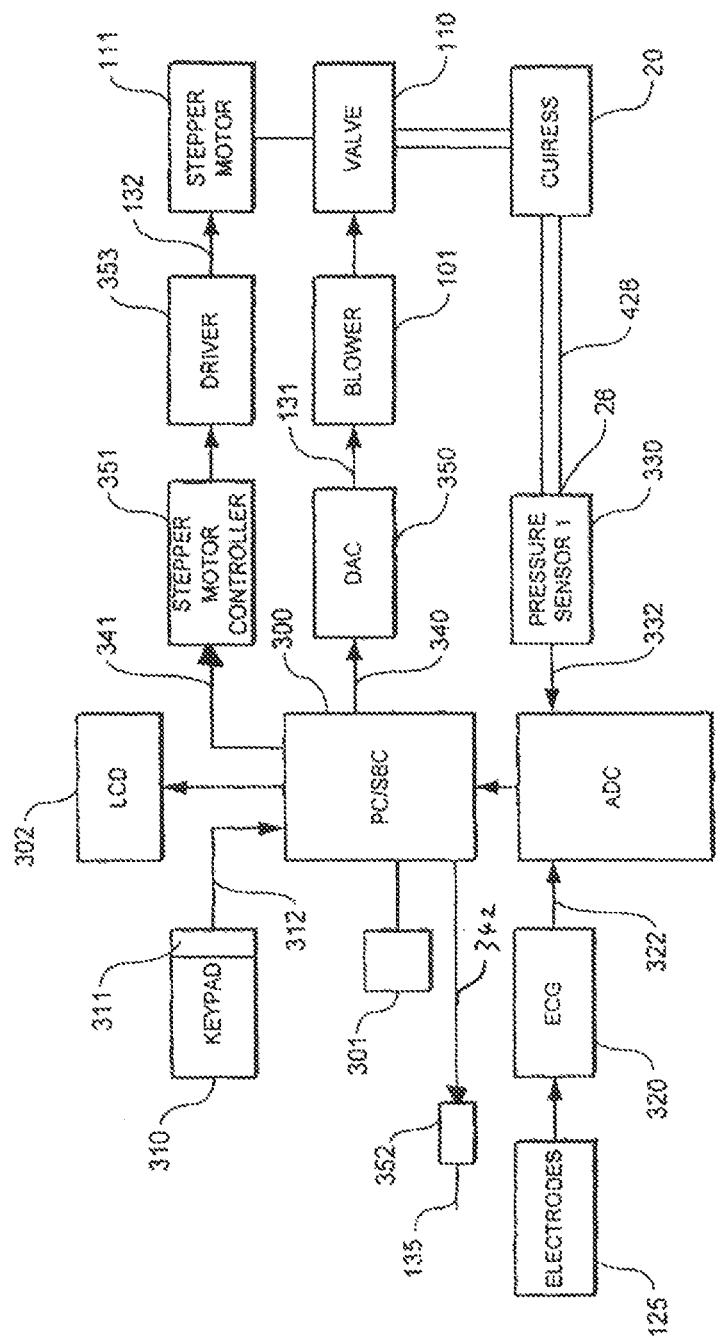
FIG. 3 shows a block schematic diagram of the ventilator of FIG. 2.

Referring now to FIG. 3, a digital processor 300 is connected to a program memory 301 storing the application programs which are run on the processor. The processor is further connected to a display device 302 which may be for example a liquid crystal display or a CRT. Control inputs to the processor are from control keys 310 via a control interface 311 and an input line 312. The processor is connected to the control port 24 for the ECG leads via an ECG interface 320 and an input bus 322. The pressure transducer input 26 is connected to a pressure transducer 330 which has an output connected to the processor via a bus 332.

The processor 300 has three output buses, 340, 341, 342. The first output bus 340 connects to a digital to analog converter 350 which typically comprises power switching circuitry and has an output forming the output power lead 131. The second bus 341 feeds a stepper motor controller 351, connected to a motor driver 353 which has an output that forms the second output lead 132. The third output bus 342 feeds a third interface circuit 352 which has an output providing the ECG trigger output line 135. Alternatively the ECG trigger line may be coupled directly to the ECG interface 320.

Although the arrangement shown has separate buses 340, 341, 342 it will be understood to those skilled in the art that a single bus could be provided having multiplexed and interleaved functionality.

It is possible to provide multiple push-buttons, one for each for function, together with numeric keys. However, in the preferred embodiment a display screen is provided with pressure lamp and selectors.

In a first mode of operation the respirator shown in FIG. 2 may provide forced respiration at a rate related to the heart rate of the patient. Thus, the chest may be arranged to be compressed at the time the heart beats so as to provide assistance to the heart.

This is achieved by the processing circuitry which operates to average the time between R wave peaks and a keypad 136 which allows the selection of a desired percentage of that time, whereupon the processing circuitry causes the valve 110 to output a positive pressure at the selected instant.

The control section 23 is also operable to set the valve to provide large amplitude pressure changes at a rate which causes the patient to become hyperventilated.

The technique for using the device is as follows:

Firstly the respirator 22 is operated cyclically to move the chest with sufficient amplitude, and sufficiently often to cause hyperventilation. This induces apnoea—i.e., it removes the body's trigger to breathe. This amplitude and frequency is achieved by sensing the peak value of pressure in the pressure line 426 and using the processor to vary the blower speed to provide the desired pressure.

Once apnoea is achieved, the respirator 22 is switched to a heart-triggered mode in which the movement of the chest is triggered by an event on the ECG waveform. In one technique, the discriminator circuitry in the respirator monitors the electrical activity of the heart and determines the timing between the peaks of the R waves of the ECG and a control is then operated to set a trigger instant for breathing at a desired percentage of the time period between successive R wave peaks.

It will be understood that breathing may be triggered with each heartbeat or alternatively a breathing rate corresponding to every two, three or four or more heartbeats may be selected as desired.

Given the prior hyperventilation, there is no longer a desire to breath and it is possible to apply external pressure to the chest to produce an "expiration hold" at a time when it is required to trigger the MRI scanner. This results in the heart being near to the chest wall which provides good results due to minimizing the distance within the body for imaging to occur. It is also possible to hold the chest at any desired position, including maximum inhalation, neutral or any intermediate position.

Due to the imposed external pressure and the previous hyperventilation, it is possible to hold the chest in the expiration position for, for example, 30 heartbeats, followed by a breathing cycle and then return to the exact location of the previous hold.

There are a number of advantages to the technique of the invention. Typically, using techniques in which the patient needs to co-operate, it may take more than 60 minutes to image the coronary arteries of the patient. Given the high cost of MRI scanners and of the staff required to operate them, this is clearly unacceptable. It is also undesirable to the patient and in any event the resolution of the scan may be insufficient to allow doctors to form an accurate diagnosis. By comparison it has been found possible to obtain high resolution images sufficient for good diagnostic quality using the present invention in less than 10 minutes. This has clear advantages to the comfort of the patient who in any event does not experience discomfort as would be caused by the need to hold breath. From the viewpoint of the hospital the speed of the technique provides a highly cost-effective procedure and the quality of the images is advantageous to the physicians who are forming a diagnosis.

In a second embodiment, the discriminator may respond to a particular waveform shape in the electrical heart waveform allowing direct triggering in response to the event which gave rise to that shape.

It will therefore be seen that the present invention by avoiding the two major disadvantages of the patient-co-operation techniques (patient breathing out at an inopportune time and a patient breathing inconsistently from breath to breath) the present invention allows for rapid high resolution imaging of coronary arteries.

As discussed above, the respirator used in the present invention may employ a cuirass sealingly engaging the chest of a patient, with air connections to a valve-blower arrangement. It will be known to those skilled in the art that conventional MRI techniques involve placing of a magnetic coil (for example having a figure-8 shape) on the chest of the patient and then introduction of the patient into a set of imaging coils. The conventional MRI scanners have a small clearance around the patient to provide the best field distribution. The use of a known cuirass may provide difficulties due to insufficient clearance and inability to adequately house the chest coil. Thus, in accordance with a further aspect of the present invention a cuirass is provided having air inlet ports to the side of the chest and having a generally raised portion over the upper part of the chest to house the coil. The seal which is preferably a seal as defined in our co-pending patent application may have a cut-out portion around its edge to allow for passage of the cabling to the coil, the dimension of the cut-out being adapted to that of the cabling so as to ensure an adequate seal.

The invention claimed is:

1. A method of operating a magnetic resonance imaging scanner for imaging the heart of a patient comprising
   inducing apnoea in the patient;
   sensing an electrical heart waveform;
   moving the chest wall of the patient to a desired location in response to said electrical heart waveform; and
   triggering the scanner to image.

2. The method of claim 1 wherein said step of moving the chest wall of the patient to a desired location comprises providing an enclosure around at least the chest of the patient and applying gas at a predetermined pressure to said enclosure.

3. The method of claim 1 wherein said step of moving the chest wall of the patient to a desired location comprises applying pressure to the outside of the chest to produce expiration.

4. The method of claim 1 wherein the apnoea is induced by hyperventilation.

5. The method of claim 1 wherein the step of inducing apnoea comprises cyclically moving the chest to cause hyperventilation.

6. The method of claim 1 further comprising the step of holding the chest wall at the desired location.

7. A magnetic resonance imaging device comprising a magnetic resonance imaging scanner, a structure in use engaging at least the chest of a patient to define, with said chest, a pressure chamber, a respirator device configured to apply cyclically varying pressures to said chamber to cause cyclic forced respiration of said patient, said forced respiration comprising successive inspiration and expiration periods that cause hyperventilation, and plural electrodes connected to said respirator device and said magnetic resonance imaging scanner configured to sense an electrical waveform of the heart of said patient, and triggering said magnetic resonance imaging scanner in accordance with said waveform, and a discriminator device configured to trigger said forced respiration in synchronism with a predetermined point of said waveform.

8. The magnetic resonance imaging device of claim 7 wherein said discriminator device is configured to determine the time period between successive maximum electrical amplitudes of said waveform, and further comprises variable timing circuitry for setting a triggering instant as a proportion of said time period.

9. The magnetic resonance imaging device of claim 7 wherein said discriminator device is configured to provide a trigger pulse in response to a predetermined characteristic of said waveform.

* * * * *